United States Patent [19]

Regal

[11] 4,163,449

[45] Aug. 7, 1979

[54] ENURESIS TREATMENT DEVICE

[76] Inventor: Robert A. Regal, 555 Kappock St., Riverdale, N.Y. 10471

[21] Appl. No.: 838,110

[22] Filed: Sep. 30, 1977

[51] Int. Cl.$^2$ .............................................. A61B 5/00
[52] U.S. Cl. ............................. 128/138 A; 200/61.05; 340/573; 340/604
[58] Field of Search ...................... 128/138 R, 138 A; 340/235, 279; 200/61.05

[56] References Cited

U.S. PATENT DOCUMENTS

| | | | |
|---|---|---|---|
| 1,749,826 | 3/1930 | Lubach | 128/138 A |
| 1,772,232 | 8/1930 | Guilder | 128/138 A |
| 3,759,246 | 9/1973 | Flack et al. | 128/138 A |
| 3,795,240 | 3/1974 | Frank | 128/2 R |
| 3,877,466 | 4/1975 | Montor | 340/279 |
| 4,052,978 | 10/1977 | Eugenio | 128/2.1 Z |

FOREIGN PATENT DOCUMENTS 1174346 12/1969 United Kingdom ................ 128/138 A

*Primary Examiner*—Dalton L. Truluck
*Assistant Examiner*—Arthur S. Rose

[57] ABSTRACT

A device which provides an aversive stimulus to a child who bed wets while asleep includes a urine detection pad of absorbent material having wire screen electrodes on both sides thereof, and an electrical circuit including an aversive alarm which is triggered when the detecting pad is moistened by a small amount of urine. A preferred embodiment of the device shuts off the alarm within a short time period if the total amount of urine deposited on the detecting pad is below a given quantity. If more than the allowable quantity of urine is deposited, the alarm continues to expose the child to the aversive stimulus. The device may also feature an adjustable threshold in its circuit to permit variation of the total quantity of urine required to continually energize the alarm, as well as selectable sensitivity of the circuit to the initial deposition of urine so that dampness caused by perspiration or humidity will not trigger the alarm.

8 Claims, 5 Drawing Figures

ENURESIS TREATMENT DEVICE

BACKGROUND OF THE INVENTION

1. Field of the Invention

The present invention relates generally to devices for detecting the occurrence of enuresis, and more particularly to devices for conditioning a child to avoid enuresis as by providing an aversive stimulus.

2. Description of the Prior Art

Apparatus for the treatment of enuresis are known, an early example appearing in an article by O. H. Mowrer entitled, "Apparatus for the Study and Treatment of Enuresis," appearing in the American Journal of Psychology, vol. 51, pp. 163–66 (1938) (hereinafter cited as Mowrer I).

The apparatus described in Mowrer I, as well as many similar devices today known and used, have as their intended function the awakening of a child "immediately upon the commencement of urination" (Mowrer I at 163). It is theorized that by providing the alarm stimulus upon urination, the alarm will condition the child to avoid bed wetting as by contraction of the sphincter whenever the child's bladder distends, thereby avoiding further urination.

Significantly, it is believed by some persons knowledgable in the field that complete awakening of the child upon each and every instance of bed wetting is necessary to develop the desired conditioning. This belief is reflected in Mowrer I wherein the author stresses the importance of such awakening. For example, Mowrer suggests that an attendant awake the child while the bell is ringing should the child not awaken thereby, and also notes a specially constructed bed which partially drops to awaken the child if the bell alone is insufficient (Mowrer I at 164).

Mowrer, in a later article entitled "Enuresis—A Method for its Study and Treatment," appearing in The American Journal of Ortho Psychiatry, vol. 8, at pp. 436–59 (1938) (hereinafter cited as Mowrer II), reiterates the requirement of an awakening stimulus to condition the child towards sphincter contraction upon bladder distention (Mowrer II at 445).

S. H. Lovibond, in an article entitled *The Mechanism of Conditioning Treatment of Enuresis*, appearing in Behavior Research and Therapy, vol. 1, pp. 17–21 (England 1963) (hereinafter cited as Lovibond), describes what he refers to as a "twin signal instrument" in which an aversive stimulus lasting for less than one second is sounded upon moistening of a detecting pad by a bed wetting child. After the stimulus sounds, a silent interval of one minute follows and then a low audible buzzer operates continuously for the purpose of summoning an attendant (Lovibond at 20). Contrary to the opinions of Mowrer, Lovibond hypothesizes that complete awakening of the child by the device is not necessary and designs his instrument accordingly. However, an attendant is required at all times to reset the instrument and change the detecting pad in response to the continually sounding, low audible buzzer thereby awakening the child. Thus, the Lovibond instrument provides only a short duration aversive alarm in the hopes that complete cessation of enuresis by the child will thereby be promoted, regardless of the amount of urine discharged by him at any one time.

It will be understood that both the Mowrer and Lovibond conditioning programs have certain attendant disadvantages and inconveniences. For example, using training techniques such as suggested by Mowrer and Lovibond, the child and all those nearby are awakened upon or soon after each instance of bed wetting, regardless of the amount.

Notably, training a child to avoid enuresis using either of the above apparatus does not provide a "reward" for the child by which the child can be taught to avoid a continuous aversive alarm by timely sphincter contraction. Neither the Mowrer nor Lovibond devices provides any change in the functioning of their respective apparatus with regard to any improvement in the child's enuretic behavior. Thus, contingent reinforcement of increased sphincter control is not possible with either device until complete control is achieved. As already stated, the aversive stimulus in the Lovibond instrument operates to sound for a time of less than one second from the very beginning of the training period to the very end. The Mowrer alarm similarly responds uniformly throughout the training period. Thus, both devices negate the possibility of any contingent reward type of training.

Another prior art device appears in U.S. Pat. No. 2,907,841, issued Oct. 6, 1959, which shows an enuresis signaling device wherein both a light and bell are activated in response to bed wetting. The bell alarm is manually disconnected by the bed wetter while the light remains on until the patented device is reset by an attendant. The device does not, however, suggest an alarm signal different from that taught by Mowrer whereby the bed wetting child is caused to be awakened and, once awake, must disconnect the alarm.

SUMMARY OF THE INVENTION

The above mentioned and other disadvantages in the known prior art are overcome by the present invention which provides an enuresis treatment device including a urine detecting pad and detection signal means coupled to the detecting pad for providing a detection signal corresponding to the state of the pad which changes in accordance with the quantity of urine discharged by a child while asleep. A noxious alarm, also included, is energized by means coupled to the signal means when the amount of urine discharged is above a first given quantity. The alarm is terminated after a short time period by alarm cut off means if the amount of discharged urine is less than a second given quantity. However, the alarm remains energized when the urine discharged is an amount greater than the second quantity.

Thus, the child obtains the "reward" of terminating the aversive stimulus once he begins to exercise control over enuresis. Until such control is exercised, the child will be exposed to a continuous aversive stimulus and caused to terminate the stimulus by turning the device off manually after each instance of uncontrolled bed wetting.

The present enuresis treatment device may further include an adjustable threshold response such as to allow a user to define the total amount of discharged urine which corresponds to the above stated second quantity, thereby providing control over the condition required for continuous energization of the alarm. Thus, the second quantity, or continuous alarm threshold of the device may at first be set relatively high so that the alarm is cut off a short time after the initial discharge of urine, unless an inordinately large amount of urine continues to be discharged by the child whereupon the alarm will remain energized. As the child begins to exercise control over urination while asleep, this threshold may be successively lowered so that the alarm is continually energized upon absorption of correspondingly lower quantities of urine by the detecting pad.

False alarms which may arise from humidity or perspiration detected by the detecting pad may also be overcome by providing sensitivity control means in the device for preventing a detection signal from being produced by the detection signal means in response to moisture in the detecting pad caused other than by the discharged urine. The sensitivity control means may include either a resistance element or a voltage source selectively switched into the circuit within the device so as to shift the level of the detection signals from the detection signal means.

DETAILED DESCRIPTION OF THE INVENTION

Figure 1:
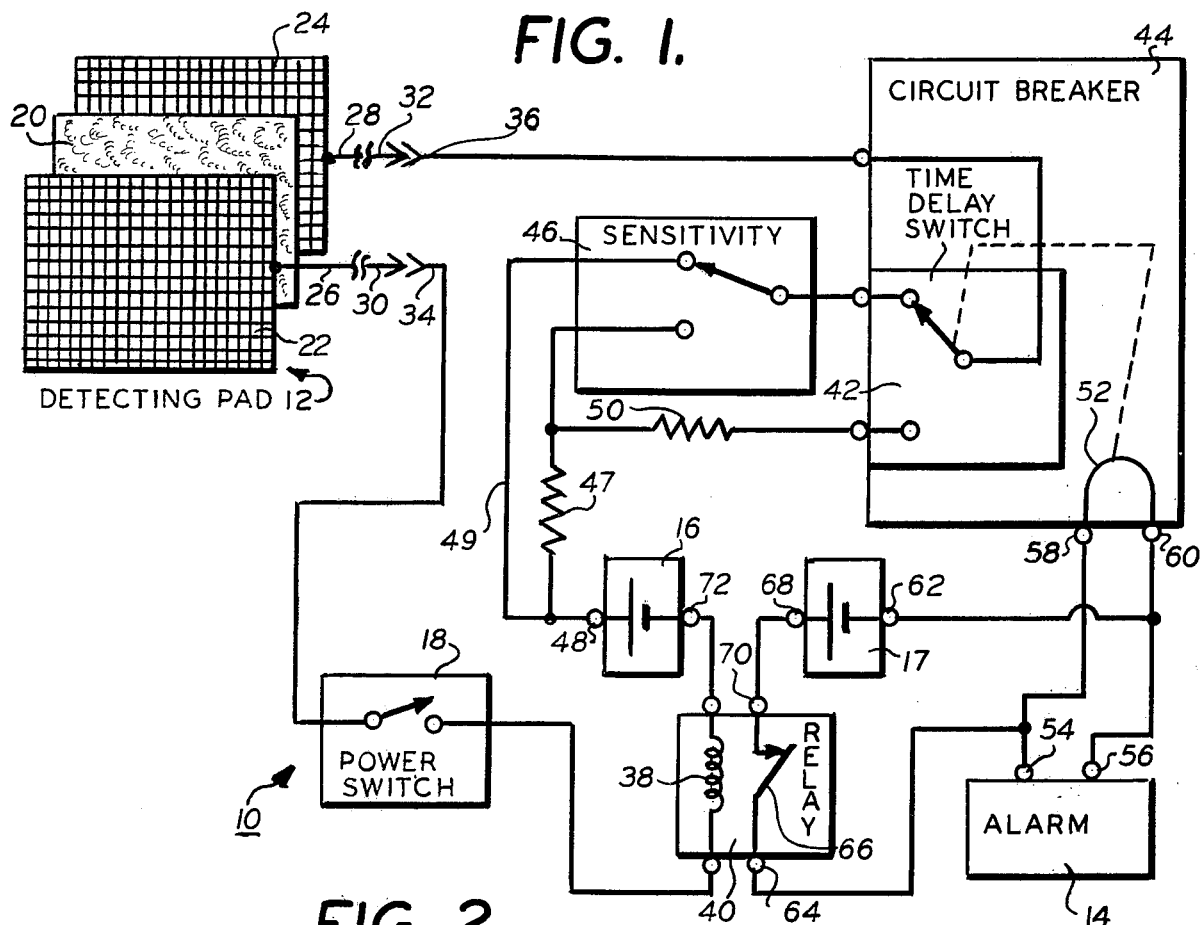
FIG. 1 is a schematic block diagram of a first embodiment of an enuresis treatment device according to the present invention.

Referring now to the drawings and initially to FIG. 1 thereof, designated generally by numeral 10 is a first embodiment of an enuresis treatment device according to the present invention. The device 10 comprises a urine detecting pad 12, an alarm 14 for providing an aversive stimulus, voltage sources 16 and 17, and circuit elements interconnecting the aforementioned components, the circuit elements to be later described.

The detecting pad 12 is arranged to be placed on a bed in which the child to be conditioned by the device 10 usually sleeps. Preferably, the detecting pad 12 is placed beneath a bed sheet at a location where urine discharged by the child while sleeping atop the bed sheet can readily pass through the sheet and be absorbed by the detecting pad 12. The alarm 14 preferably emits a noxious or aversive noise in response to the bed wetting such as to affect the bed wetter by either subjecting him to a continuously sounding noxious sound, or by "rewarding" him upon his learning to avoid further bed wetting by terminating the noxious sound automatically as will be described hereinafter. This procedure of avoidance conditioning is an important feature of the present invention and greatly enhances its effectiveness in a manner not heretofore suggested by the known prior enuresis treatment devices.

While the alarm 14 is described as preferably emitting an aversive noise, it will be understood that other means for producing aversive stimuli, e.g., mild electric shock, may be used as well without departing from the effectiveness of the present invention as an avoidance conditioning device.

Continuing now with reference to FIG. 1, voltage source 16, preferably a battery provided by the user and connectable to the device 10 as by unshown terminal leads, supplies power for a urine detection portion of the device 10. Voltage source 17, also preferably provided and connectable by the user, powers an alarm portion of the device 10. A power switch 18 is preferably provided to avoid wasteful drainage of the voltage sources 16, 17 when the device 10 is not being used. It has been found, for example, that suitable voltage sources 16, 17 for the device 10 may comprise nine volt alkaline batteries, such as Mallory MN1604 or equivalent.

The other elements comprising the device 10 and their respective operations will now be described in further detail.

Detecting pad 12 preferably comprises an absorbent pad 20 which is sandwiched between, and normally acts to electrically insulate, a pair of aluminum wire cloth screens 22, 24 from one another.

For purposes of illustration, the elements comprising detecting pad 12 are shown separated from one another. It will be apparent, however, that the screens 22, 24 are tightly secured against respective sides of the cloth 20 as by, for example, stitching with cotton thread.

Connected to each of the screens 22, 24 are conducting leads 26, 28 which preferably terminate with connectors 30, 32, respectively. It will be understood that the connecting leads 26, 28 are preferably of narrow gauge and easily flexible so as to allow for their routing from the wire screens 22, 24 under the aforementioned bed sheet to connect with the remainder of the device 10 which may be located atop a table near the bed being used. Also, the leads 26, 28 are preferably well insulated from one another to avoid inadvertent electrical contact therebetween such as to cause false alarms to be emitted by the device 10.

The leads 26, 28 from the detecting pad 12 are connected to the remainder of the device 10 by way of the lead connectors 30, 32 which are mated with corresponding connectors 34, 36 provided on the device 10. A detection current path is defined in the device 10 between the device connectors 34, 36, this path including power switch 18, a sensing coil 38 of a relay 40, voltage source 16, a sensitivity switch unit 46, and a time delay switch 42 which is actuable together with and contained in a circuit breaker 44, circuit breaker 44 being shown in a set condition in FIG. 1.

It will be seen that sensitivity switch 46 acts to select either a direct connection 49 between the set time delay switch 42 and one terminal 48 of voltage source 16, or a resistance element 47 between the set time delay switch 42 and voltage source 16 depending upon the state of switch 46.

The alarm 14 has both its terminals 54, 56, respectively, connected to the current sensing terminals 58, 60 on circuit breaker 44. Also, one of the alarm terminals 56 is connected to one side 62 of voltage source 17 and the other alarm terminal 54 is connected to one of the terminals 64 of a normally open switch 66 in relay 40. The other side 68 of voltage source 17 connects to the remaining terminal 70 of the relay switch 66, and relay coil 38 is connected in series between power switch 18 and the remaining terminal 72 of voltage source 16.

It will now be apparent that an initial urine detection current will be induced to flow in the circuit defining the detection portion of device 10 upon the completion of the current path between the wire screens 22, 24, as by the absorption of urine by the sandwiched absorbent pad 20. This resulting initial current flow through the sensing coil 38 of relay 40 causes the relay switch 66 to close, thereby connecting the voltage source 17 directly across the terminals 54, 56 of the alarm 14 and current sensing terminals 58, 60 of the circuit breaker 44, respectively.

It will be appreciated that a relatively heavy current is caused to flow through current sensitive element 52 in circuit breaker 44 when the alarm 14 is energized so that the element 52 opens and the circuit breaker 44 is thereby tripped within a relatively short time period of preferably between one to three seconds. Tripping of the circuit breaker 44 causes internal actuation of the time delay switch 42 within the circuit breaker 44, as noted above, thereby introducing resistance element 50 into the above mentioned detection current path.

The resistance element 50, once switched into the detection current path, will operate to decrease the detection current flow since the potential of voltage source 16 in the detection circuit remains relatively constant. Depending on the initial value of the detection current, this reduction thereof may or may not be such as to maintain the switch 66 in relay 40 closed.

It will be understood that the initial detection current value itself depends on the conductivity of the absorbent pad 20 after its absorption of urine, i.e., a change in state of the detecting pad 12, such conductivity being proportional to the amount of urine deposited on the pad 12 by the enuretic child.

Thus, if a sufficiently large amount of urine is discharged and absorbed in the detecting pad 12, the initial detection current produced will be relatively high and, further, the reduction thereof caused by the insertion of resistance element 50 in its path will not be sufficient to deactivate the relay 40. In such case, the voltage source 17 remains connected across the alarm terminals 54, 56, the source 17 no longer being drained by way of the current sensitive element 52 in the circuit breaker 44 as element 52 remains open until the circuit breaker 44 is manually reset.

The alarm 14, when continually energized by the voltage source 17, will provide a steady aversive stimulus to the enuretic child so as to fully awaken him. Upon awakening, the child may turn off the alarm 14 by way of the power switch 18. The child or someone else then removes the absorbent pad 20 from between the wire screen electrodes 22, 24 of the detecting pad 12, and either washes and dries the absorbent pad 20 or replaces it with another similar absorbent pad before the child resumes sleep with the power switch 18 in device 10 again turned on.

As pointed out above, an important feature of the present invention is the provision of means in the detection portion of the device 10 for disconnecting the alarm 14 from the voltage source 17 if the amount of urine absorbed into the detecting pad 12 is less than a given amount, thereby, in effect, rewarding the enuretic child by terminating an aversive stimulus once he begins to exercise control over urination while still asleep. Thus, as mentioned above, it is possible for the switch 66 in relay 40 to open and disconnect the voltage source 17 from the alarm 14 in the event that a relatively slight amount of urine is absorbed in the pad 12. In such cases the detection current which flows after the circuit breaker 44 is tripped, and resistance element 50 is switched into the detection current path by switch 42, is insufficient to energize the relay coil 38. Relay switch 66 then opens and voltage source 17 is thereby removed from alarm 14.

Thus, although the alarm 14 is first energized upon a relatively slight discharge of urine onto the detecting pad 12, the alarm 14 will cease to operate upon the tripping of the circuit breaker 44 after a time period of preferably one to three seconds, depending on the particular type of circuit breaker 44 which is used. In the preferred embodiment, the circuit breaker 44 is manufactured by Heinemann Company, Trenton, N.J., Cat. No. SES-998-2, Part No. JA1-B2, six volts D.C. Of course, any other circuit breaker having the electrical characteristics and internal co-acting switch 42 as in the aforesaid preferred circuit breaker 44 may be used.

Should the discharge of urine be sufficiently slight so as to allow the alarm 14 to become de-energized upon tripping of the circuit breaker 44, as above described, it will be apparent that although the enuretic child may not be fully awakened, and the circuit breaker 44 is not reset so as to remove the resistance element 50 from the detection current path, the alarm 14 may still later be energized by the discharge of an additional amount of urine onto the detecting pad 12 which imparts additional conductivity to the absorbent pad 20, thereby providing an increased flow of detection current through the relay coil 38 which is sufficient to overcome the effect of resistance element 50. Therefore, the relay 40 will again be actuated in response to the increased detection current, whereupon the switch 66 will again close to connect voltage source 17 across the alarm 14. Thereafter, the alarm 14 will remain energized to awaken the enuretic child.

The particular preferred alarm used is made by AristoCraft, model H-60, six volt, 200 ma. Of course, any other equivalent alarm unit can be used provided it produces a sufficiently aversive sound.

It is further noted that for proper operation of the device 10, before its being put to use, the circuit breaker 44 should be set and the absorbent pad 20 be dry so as to allow for maximum sensitivity of the device 10 to an initial discharge of urine by the enuretic child.

Another feature of the present invention is the provision of means whereby the sensitivity of the device 10 after circuit breaker 44 is tripped, and co-acting time delay switch 42 is actuated, may be controlled by a user so as to define the total amount of urine which, when absorbed into detecting pad 12, will result in continuous energization of alarm 14 to fully awaken the child being treated.

Figure 2:
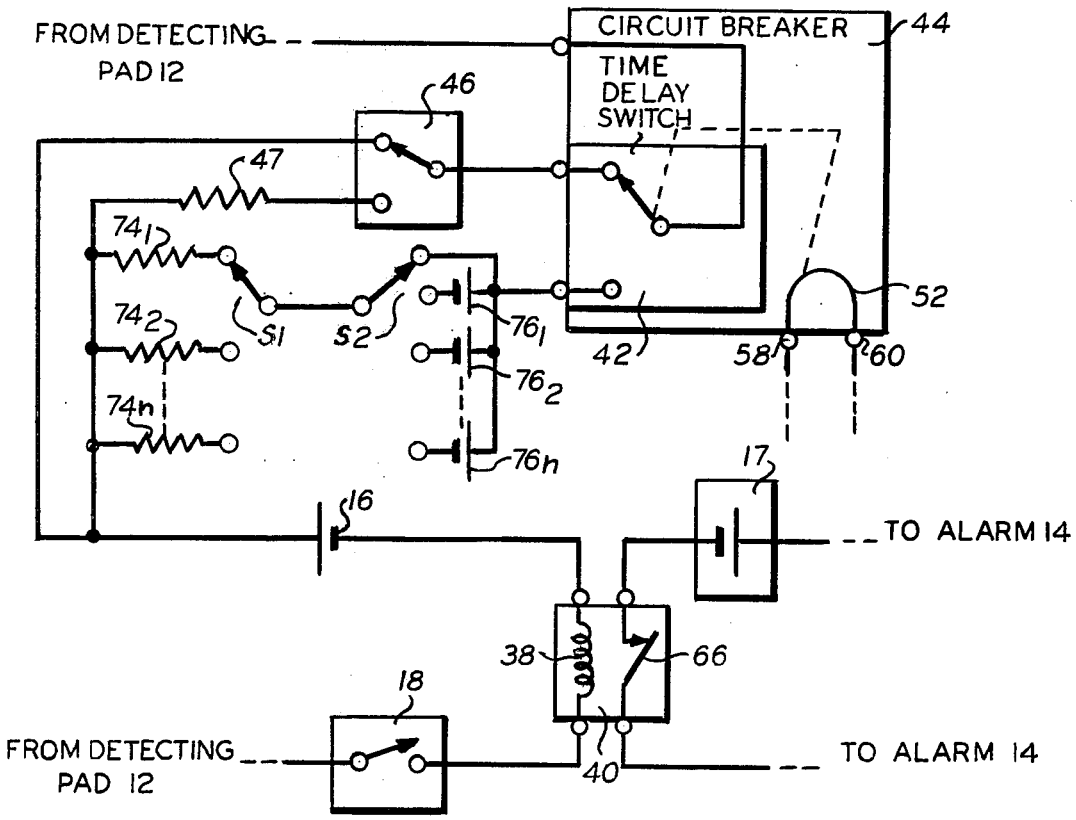
FIG. 2 is a schematic block diagram of a modification of a portion of the enuresis treatment device of FIG. 1 according to the present invention.

FIG. 2 shows a portion of FIG. 1 as modified to include the aforesaid means for changing the threshold of the device 10 at which alarm 14 remains continually energized after actuation of time delay switch 42. Referring to FIG. 2, it will be seen that resistance element 50 is replaced by switch selected resistance elements $74_1$, $74_2 \ldots 74_n$. Also, in addition to voltage source 16, it is possible to switch select any one of voltage sources $76_1$, $76_2 \ldots 76_n$ into the detection current path. Switches S1, S2, for selecting resistance elements 74 and voltage sources 76, respectively, are shown in FIG. 2 as being preferably independently actuable in order to provide the greatest amount of threshold adjustability. However, switches S1, S2 may be coactuable as well, if desired.

It will be apparent that the modification of the device 10 as shown in FIG. 2 provides a detection current path similar to that of the device 10 in FIG. 1 before circuit breaker 44 is tripped and time delay switch 42 is actuated. Specifically, detection current produced upon the initial deposition of urine onto detecting pad 12 by the enuretic child flows through time delay switch 42, sensitivity switch unit 46 and voltage source 16 to energize the relay coil 38 when the power switch 18 is closed.

Upon actuation of time delay switch 42, however, the detection current flows through a path including the selected resistance element 74 and, if also selected, an additional voltage source 76.

The modification in FIG. 2 therefore provides a significant advantage in use of the device 10 of FIG. 1 in that during the initial stages of treatement of an enuretic child, the total amount of urine required to be absorbed in the detecting pad 12 to continually energize alarm 14 and awaken the child, may be set by the user to correspond to the relatively large amount which the child normally discharges when asleep. This initial setting of the device 10 according to FIG. 2 can be made, for example, by switching successively lower valued resistance elements 74 into the circuit until the alarm 14 sounds continuously, after time delay switch 42 is actuated, i.e., circuit breaker 44 is tripped upon the first bedwetting by the child.

In order to promote conditioning of the child to avoid enuresis as much as possible, a "reward" system of conditioning is preferred in which the device of FIG. 2 is adjusted to emit a continuous aversive stimulus to the child in response to the initially large amounts of urine typically discharged at the beginning of the training program. Therefore, the device should at first be adjusted so that alarm 14 sounds continuously after the usual amount of bedwetting by the child, as explained above, but will be cut off once the child begins to exercise some control over enuresis.

A next lower value resistance element 74 may, for example, be switched into the circuit of FIG. 2 so as to lower the threshold of the device 10 at which alarm 14 is continually energized, once the child begins to respond. Now, the child will be fully awakened upon the discharge of a lesser quantity of urine onto the detecting pad 12 and will thereby learn to exercise still further control over nocturnal enuresis. Eventually, the alarm 14 will sound only during the initial one to three second time period before circuit breaker 44 trips and causes alarm 14 to be cut off, the amount of urine finally being discharged by the child, if any, not being sufficient to overcome the effect of the last selected, lowest valued resistance element 74.

As shown in FIG. 2, it may be desirable to select a particular voltage source 76 in series with the selected resistance element 74 in the detection current path. This selection of voltage sources 76 provides an even greater degree of adjustability over the threshold of the device 10 at which alarm 14 remains continually energized in response to a particular quantity of urine absorbed in detecting pad 12.

A further feature of the present invention is the provision of means for controlling the initial sensitivity of the device 10 to deposits of urine on the detecting pad 12, such control being desirable to prevent false alarms caused by, for example, perspiration from the enuretic child or humidity and dampness in the environment where the device 10 is used.

Sensitivity control means appears, in FIG. 1, by way of the switch unit 46, resistance element 47 and conductor 49. As shown in FIG. 1, the sensitivity switch unit 46 is in a position such as to provide maximum sensitivity of the device 10 to urine initially discharged onto the detecting pad 12 and absorbed in the absorbent pad 20. Should dampness be imparted to the absorbent pad 20 by way of perspiration, humidity or some condition other than the discharge of urine, such as would cause energization of the alarm 14, the sensitivity of the device 10 can be accordingly reduced by switching the sensitivity switch unit 46 to a position whereat resistance element 47 is connected in the detection current path in the device 10. Of course, the particular switching arrangement shown is for purposes of illustration only, and any other switching arrangement in which one or more resistance elements can be selectively inserted in the signaling current path may be used.

The sensitivity control means described above can be advantageously employed within prior existing enuresis treatment devices to thereby expand their usefulness. An arrangement such as this is shown and described later in regard to FIG. 4.

Figure 3:
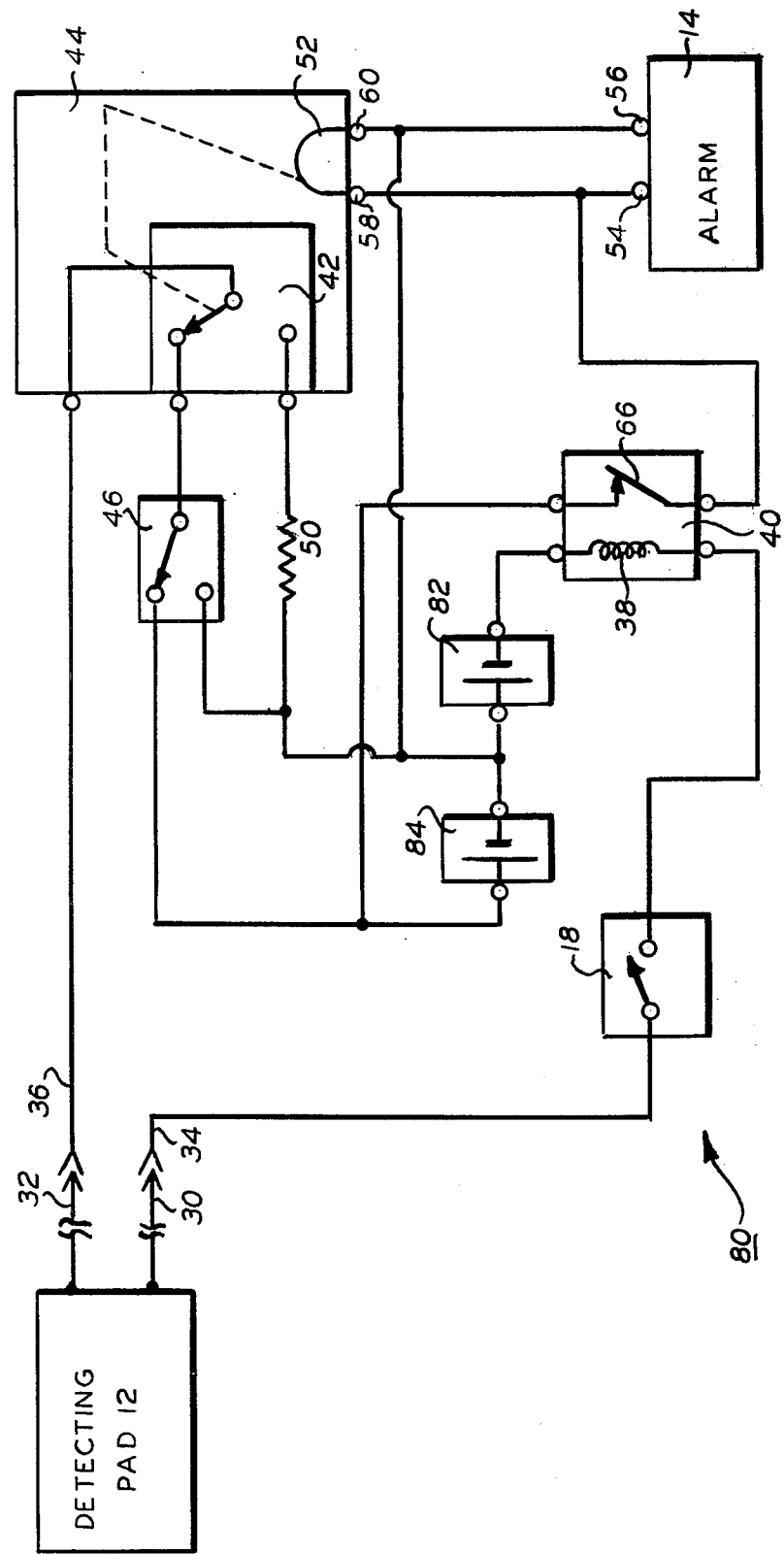
FIG. 3 is a schematic block diagram of a second embodiment of an enuresis treatment device according to the present invention.

Referring now to FIG. 3, an embodiment of the present invention incorporating a different form of sensitivity control means than that shown in FIG. 1 is designated generally by numeral 80. Elements included in the device 80 which are similar to those in the device 10 of FIG. 1 are correspondingly numbered.

The device 80 in FIG. 3 employs voltage sources 82, 84 in such a manner as to provide two levels of sensitivity of the device 80 to the initial urine detection current flow produced in response to the deposition of urine on the detecting pad 12. The voltage source 84 always acts to provide power for energization of the alarm 14, and can also be switched into the detection current circuit path by way of sensitivity switch 46. Voltage source 82 is used only for providing detection current, either alone or in combination with source 84 depending on the state of switch 46. With switch 46 in the position as shown in FIG. 3, maximum sensitivity of device 80 to the initial detection current will be obtained.

It will be appreciated that any drop of voltage in voltage source 84 which is normally used for supplying current to energize alarm 14 will result in a corresponding decrease in the maximum initial sensitivity obtainable for the device 80 to the absorption of urine in detecting pad 12, such decreased sensitivity not being desirable. However, it will be appreciated that if the rated voltage of voltage source 84 is higher than, e.g., twice as high as that of voltage source 82, reduction of the voltage obtainable from source 84 over a period of use of device 80 will not significantly affect the maximum selected sensitivity of the device 80 as shown in FIG. 3. It has been found, for example, that the voltage source 82 may comprise a 4½ volt (three 1½ volt AA alkaline cells) battery source with the source 84 comprising a standard 9 volt alkaline cell.

Thus, in operation, the sensitivity of the device 80 is controlled by switching the voltage source 84 in or out of the path of detection current flow, this current path leading from detecting pad 12 through device connector 34, power switch 18, relay coil 38, voltage source 82, voltage source 84 if switched into the path by switch 46, switch 42 in circuit breaker 44 and back to detecting pad 12 by way of device connector 36.

Both methods of controlling the initial sensitivity of the present devices 10, 80 to the discharge of urine by the enuretic child, as described in connection with FIGS. 1 and 3, respectively, may be usefully employed in any enuresis treatment device which uses a detecting pad such as the pad 12 described above, and an alarm which is energized in response to a current flow through the pad and circuitry in the device which energizes the alarm in response to absorption by the pad of a quantity of dicharged urine.

Figure 4:
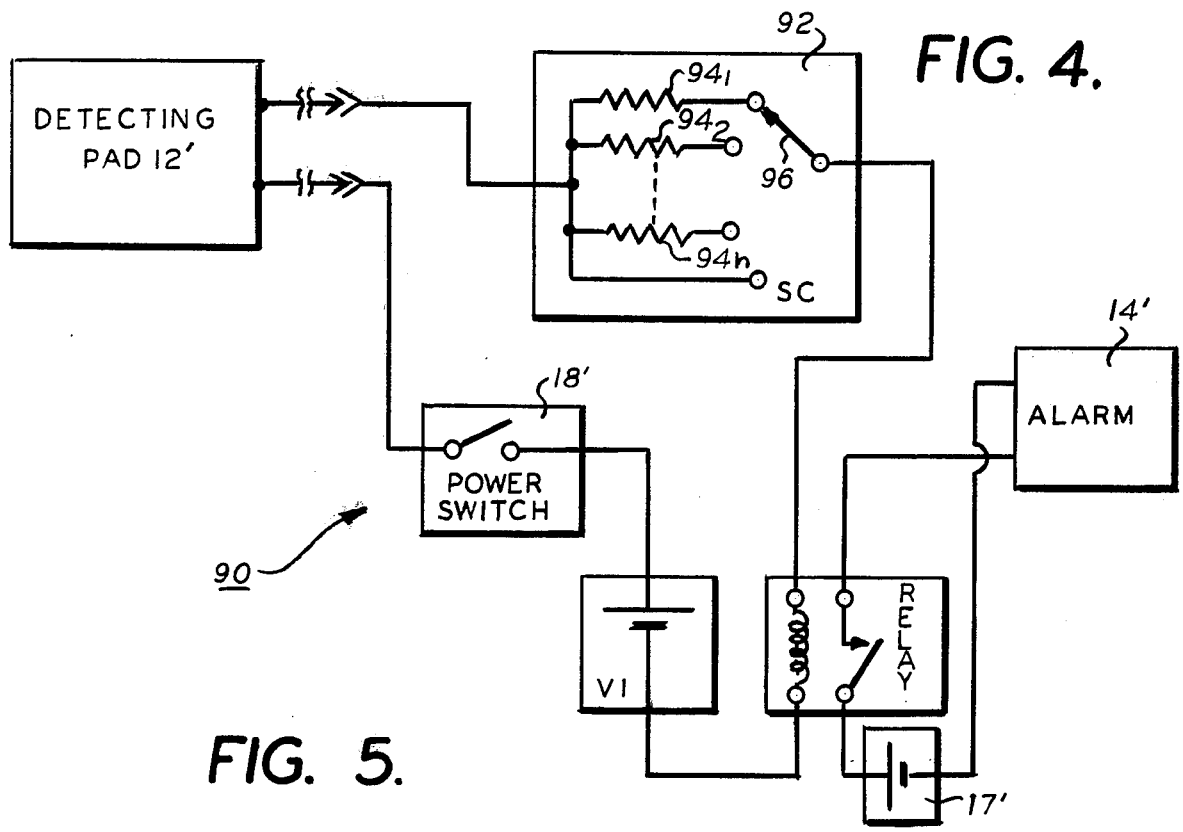
FIG. 4 is a schematic block diagram of a third embodiment of an enuresis treatment device according to the present invention.

For example, as shown in FIG. 4, an enuresis treatment device 90 may include a switch unit 92 operative to insert a selected one of resistors $94_1, 94_2 \ldots 94_n$, or a short circuit in series with detection current path of the device 90 when the detecting pad 12' is connected to the device 90 as shown.

The resistors $94_1, 94_2 \ldots 94_n$ are preferably of values which successively decrease as switch contact 96 is rotated towards shorting terminal SC. It will be understood that maximum sensitivity for the device 90 is obtained when switch contact 96 is connected to the shorting terminal SC, and that successively decreasing sensitivities can be obtained as by rotating switch contact 96 away from shorting terminal SC to connect to successively higher value resistance elements 94.

Figure 5:
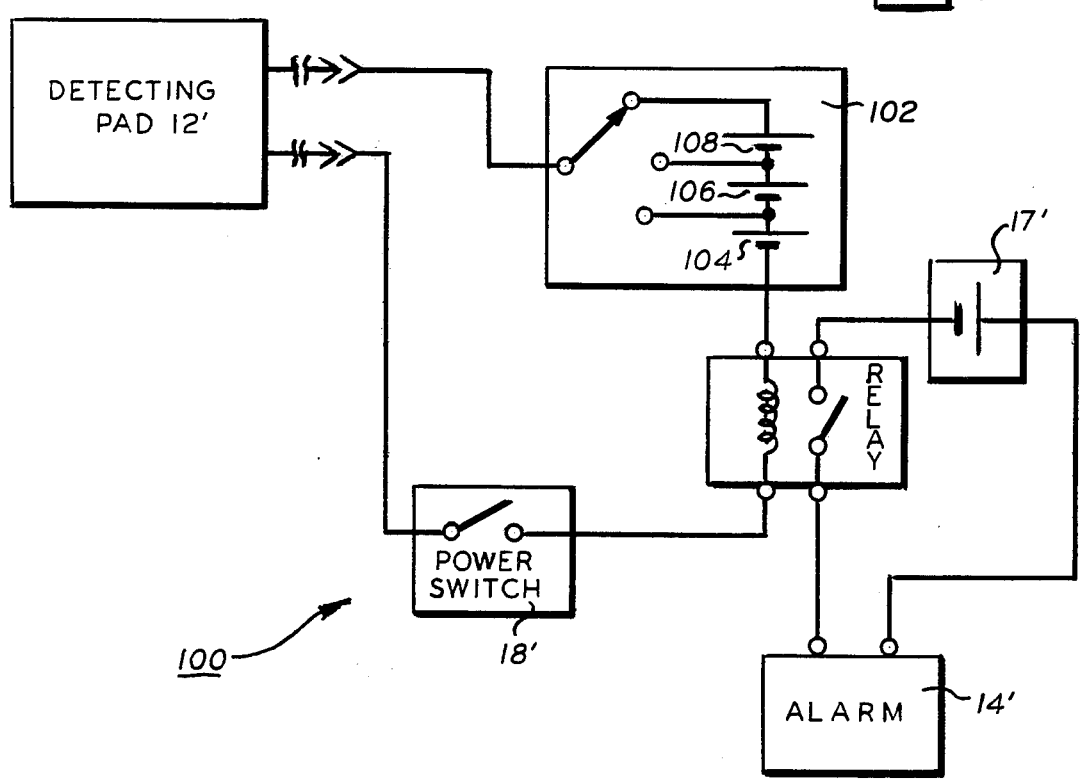
FIG. 5 is a schematic block diagram of a fourth embodiment of an enuresis treatment device according to the present invention.

The method of controlling the initial sensitivity of the device 80 in FIG. 3, wherein the two voltage sources 82, 84 and switch 46 are arranged to selectably connect voltage source 84 into the detection current path, may be embodied within an enuresis treatment device 100 as shown in FIG. 5.

A voltage selection switch unit 102 is provided in the device 100 for switching combinations of voltage sources 104, 106 and 108 into the detection current path in the device 100. It will be understood that any number of voltage sources may be combined by a switch unit such as 102, and that the three sources 104, 106 and 108 are shown for purposes of illustration only.

Using the device 100, it will be apparent that the sensitivity thereof to deposits of urine on the detecting pad 12' may be increased by switching a successively greater number of the voltage sources 104, 106 and 108, which are connected in series adding relationship, into the detection current path of device 100. In the position shown in FIG. 5, all of the sources 104, 106 and 108 are connected in the detecting current path to yield maximum sensitivity for the device 100.

The rated voltage of each of these sources may be selected so as to provide any desired degree of adjustment in sensitivity at each position of the switch 102.

Variations and modifications of the enuresis treatment device according to the present invention will be apparent to a worker skilled in the art and all such variations and modifications are intended to be included within the spirit and scope of the present invention. For example, the relays 40 disclosed in the various embodiments herein are shown and described as being conventional electromagnetic relays. Alternatively, these relays may, for example, comprise equivalent solid state devices operative to detect a flow of current or a voltage produced by a flow of current, and to connect a voltage source to energize the alarms herein disclosed. Further, although the alarms have been disclosed herein as producing an aversive noise when energized, other alarms may be used which produce other aversive stimuli to the enuretic child such as, for example, mild electric shock as mentioned above.

Having thus fully described my present invention, what is claimed as new and desired to be secured by Letters Patent is:

1. A device for treating an enuretic person by conditioning said person to avoid nocturnal bed wetting, said device comprising:

a urine detecting pad arranged to be placed underneath said person while asleep for absorbing urine discharged by said person, said pad changing its state in corresponding relationship with the quantity of urine absorbed by said pad;

detection signal means coupled to said detecting pad for producing detection signals corresponding to the state of said urine detecting pad;

an alarm for providing an aversive stimulus to said person;

alarm energization means coupled to said alarm and said detection signal means for energizing said alarm when said detection signals are above a first level corresponding to a first quantity of said absorbed urine; and alarm cutoff means coupled to said alarm and said detection signal means for disabling said alarm after a particular elapsed time when said detection signals are below a second level corresponding to a second quantity of said absorbed urine, and for allowing said alarm to remain energized when said detection signals are above said second level;

whereby said alarm is energized only over a sufficient time to provide an aversive stimulus to said person while asleep when less than said second quantity of urine is discharged by said person, and said alarm remains energized when more than said second quantity of urine is discharged by said person to thereby awaken said person.

2. A device according to claim 1, further including second level threshold control means coupled within said detection signal means for selectably adjusting the second level of said detection signals at which said alarm remains continually energized after said alarm cutoff means is actuated.

3. A device according to claim 2, wherein said threshold control means includes a selected resistance element.

4. A device according to claim 2, wherein said threshold control means includes a selected voltage source.

5. A device according to claim 1 further including sensitivity control means coupled within said detection signal means for selectably shifting the level of said detection signals to prevent alarm energization in response to moisture in said detecting pad caused other than by said discharged urine.

6. A device according to claim 5 wherein said sensitivity control means comprises a selected resistance element.

7. A device according to claim 5 wherein said sensitivity control means comprises a selected voltage source.

8. A device in accordance with claim 1 wherein said alarm cutoff means comprises means which are armed when said first level detection signal is initially detected for initially arming said alarm, said arming means remaining armed after said alarm is disabled after said particular elapsed time to enable said alarm to be energized to provide a continuous alarm whenever said detection signals detected by said detection signal means are above said second level, whereby said device remains continually alert to respond to the discharge and absorption of said quantity of urine by said detecting pad even if said second quantity of discharge occurs at a discontinuous time after said first level detection signal is initially detected.

* * * * *